US010402972B2

United States Patent
Kuusela et al.

(10) Patent No.: US 10,402,972 B2
(45) Date of Patent: Sep. 3, 2019

(54) METHODS AND SYSTEMS FOR RADIATION DOSE ESTIMATION

(71) Applicant: VARIAN MEDICAL SYSTEMS INTERNATIONAL AG, Cham (CH)

(72) Inventors: Esa Kuusela, Espoo (FI); Lauri Halko, Helsinki (FI)

(73) Assignee: VARIAN MEDICAL SYSTEMS INTERNATIONAL AG (CH)

( * ) Notice: Subject to any disclaimer, the term of this patent is extended or adjusted under 35 U.S.C. 154(b) by 197 days.

(21) Appl. No.: 15/668,712

(22) Filed: Aug. 4, 2017

(65) Prior Publication Data

US 2019/0043187 A1   Feb. 7, 2019

(51) Int. Cl.
| | |
|---|---|
| A61B 6/00 | (2006.01) |
| A61B 6/03 | (2006.01) |
| A61N 5/10 | (2006.01) |
| G06T 7/00 | (2017.01) |
| G06T 7/11 | (2017.01) |

(52) U.S. Cl.
CPC .......... *G06T 7/0012* (2013.01); *A61B 6/032* (2013.01); *A61B 6/542* (2013.01); *A61N 5/103* (2013.01); *G06T 7/11* (2017.01); *G06T 2207/10116* (2013.01)

(58) Field of Classification Search
CPC ......... G06T 7/0012; G06T 7/11; A61B 6/032; A61B 6/542; A61B 6/103
See application file for complete search history.

(56) References Cited

U.S. PATENT DOCUMENTS

| | | | |
|---|---|---|---|
| 2010/0215141 A1* | 8/2010 | Kondo | A61B 6/032 378/16 |
| 2013/0136328 A1* | 5/2013 | Jansen | G06T 11/005 382/131 |
| 2013/0223588 A1* | 8/2013 | Kurochi | A61B 6/06 378/19 |

FOREIGN PATENT DOCUMENTS

| | | |
|---|---|---|
| WO | 2014145452 A1 | 9/2014 |
| WO | 2017023105 A1 | 2/2017 |

OTHER PUBLICATIONS

International Search Report and Written Opinion of the International Searching Authority, International application No. PCT/CN2018/045279, dated Nov. 12, 2018.

* cited by examiner

*Primary Examiner* — Kim Y Vu
*Assistant Examiner* — Molly Delaney
(74) *Attorney, Agent, or Firm* — Su IP Consulting (57) ABSTRACT

Example methods and systems are provided to perform radiation dose estimation for a target object. In one example, radiation dose estimation may include obtaining projection image data acquired using an imaging system, generating partially reconstructed volume image data based on the projection image data, and generating a partition of the projection image data. The partially reconstructed volume image data may be associated with a first region of a total radiation field. The partition may be associated with a second region of the total radiation field that is located before the first region from a direction of a radiation source. Radiation dose data may be estimated for the target object based on the partially reconstructed volume image data associated with the first region and the partition associated with the second region.

21 Claims, 7 Drawing Sheets

METHODS AND SYSTEMS FOR RADIATION DOSE ESTIMATION

BACKGROUND

Unless otherwise indicated herein, the approaches described in this section are not prior art to the claims in this application and are not admitted to be prior art by inclusion in this section.

Radiotherapy is an important part of a treatment for reducing or eliminating unwanted tumors from patients. Unfortunately, applied radiation does not inherently discriminate between an unwanted tumor and any proximal healthy structures such as organs, etc. This necessitates careful administration to restrict the radiation to the tumor (i.e., target). Ideally, the goal is to deliver a lethal or curative radiation dose to the tumor, while maintaining an acceptable dose level in the proximal healthy structures. However, in practice, there are various challenges associated with radiation dose estimation to deliver radiation doses that achieve this goal.

SUMMARY

According to examples of the present disclosure, methods and systems for radiation dose estimation are provided. An example method may include obtaining projection image data acquired using an imaging system, generating partially reconstructed volume image data based on the projection image data, generating a partition of the projection image data, and estimating radiation dose data for a target object based on the partially reconstructed volume image data associated with the first region and the partition associated with the second region.

According to examples of the present disclosure, the projection image data may be acquired by projecting radiation from a radiation source through a target object positioned within a total radiation field of the imaging system. The partially reconstructed volume image data may be associated with a first region of the total radiation field. The partition may be associated with a second region of the total radiation field that is located before the first region from a direction of the radiation source.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Figure 1:
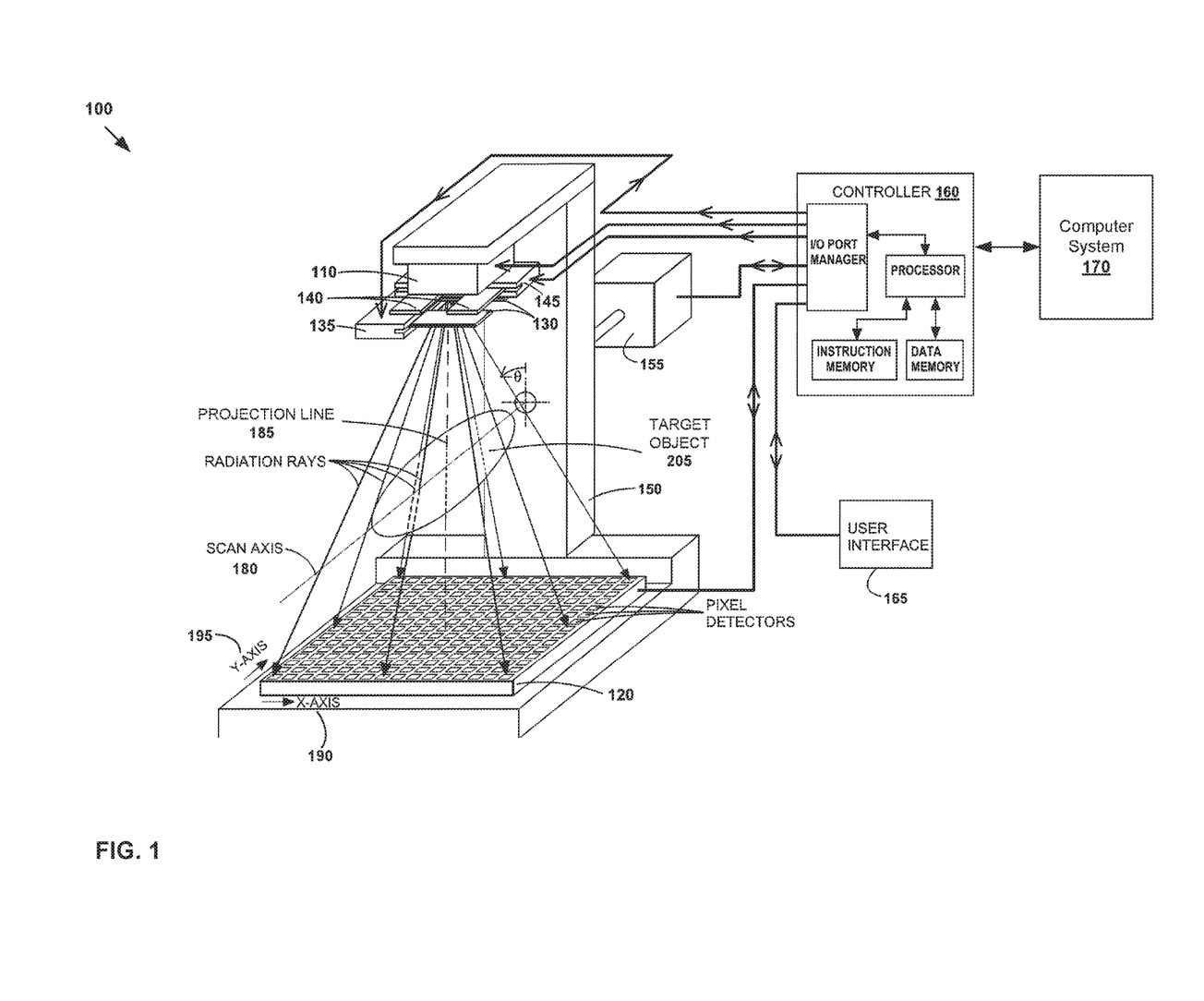
FIG. 1 is a schematic diagram illustrating an example imaging system.

FIG. 1 is a schematic diagram illustrating example imaging system 100. Although one example is shown, imaging system 100 may have alternative or additional components depending on the desired implementation in practice. In the example FIG. 1, imaging system 100 includes radiation source 110; detector 120 having pixel detectors disposed opposite to radiation source 110 along a projection line (defined below; see 185); first set of fan blades 130 disposed between radiation source 110 and detector 120; and first fan-blade drive 135 that holds fan blades 130 and sets their positions. The edges of fan blades 130 may be oriented substantially perpendicular to a scan axis (defined below; see 180), and are substantially parallel with the trans-axial dimension (defined below) of detector 120.

Imaging system 100 may further include second set of fan blades 140 disposed between radiation source 110 and detector 120, and second fan-blade drive 145 that holds fan blades 140 and sets their positions. The edges of fan blades 140 may be oriented substantially parallel with a scan axis (defined below; see 180), and are substantially perpendicular to the axial dimension (defined below) of detector 120. Fan blades 130 and 140 are generally disposed closer to the radiation source 110 than detector 120. They are normally kept wide open to enable the full extent of detector 120 to be exposed to radiation, but may be partially closed in certain situations.

Imaging system 100 further includes gantry 150 that holds at least radiation source 110, detector 120, and fan-blade drives 135 and 145 in fixed or known spatial relationships to one another, mechanical drive 155 that rotates gantry 150 about target object 105 disposed between radiation source 110 and detector 120, with target object 105 being disposed between fan blades 130 and 140 on the one hand, and detector 120 on the other hand. The term "gantry" has a broad meaning, and covers all configurations of one or more structural members that can hold the above-identified components in fixed or known (but possibly movable) spatial relationships. For simplicity in FIG. 1, gantry housing, gantry support and fan-blade support are not shown.

Additionally, imaging system 100 includes controller 160, user interface 165, and computer system 170. Controller 160 may be electrically coupled to radiation source 110, mechanical drive 155, fan-blade drives 135 and 145, detector 120, and user interface 165. User interface 165 may be configured to enable a user to at least initiate a scan of target object 105, and to collect or measure two-dimensional (2D) projection image data from detector 120. User interface 165 may be configured to present graphic representations of the projection image data. Computer system 170, which is coupled to controller 160, may be configured to perform various operations (e.g., data processing, dose estimation, etc.) that will be described in more detail below. Throughout the present disclosure, the term "projection image data" may be used interchangeably with "projection data," "projection (s)", "radiographic projection(s)" and "projection image(s)." The term "projection angle" may also be used interchangeably with "projection view."

In imaging system 100, gantry 150 may be configured to rotate about target object 105 during a scan such that radiation source 110, fan blades 130 and 140, fan-blade drives 135 and 145, and detector 120 circle around target object 105. More specifically, gantry 150 may rotate these components about scan axis 180 that intersects with (and is typically perpendicular to) projection line 185. Target object 105 is generally aligned in a substantially fixed relationship to scan axis 180. The configuration provides a relative rotation between projection line 185 on one hand, and scan axis 180 and target object 105 aligned thereto on the other hand, with the relative rotation being measured by an angular displacement value θ. Mechanical drive 155 may be coupled to the gantry 150 to provide rotation upon command by controller 160. The array of pixel detectors on detector 120 may be periodically read to acquire the projection image data.

Detector 120 has X-axis 190 and Y-axis 195, which are perpendicular to each other. Detector 120 may be oriented such that its Y-axis 195 is parallel to scan axis 180. For this reason, Y-axis 195 may also be referred to as the axial dimension of detector 120, and X-axis 190 as the trans-axial dimension, or lateral dimension. X-axis 190 is perpendicular to a plane defined by scan axis 180 and projection line 185, and Y-axis 195 is parallel to this same plane. Each pixel (X, Y) on detector 120 is assigned a discrete X-coordinate ("X") along X-axis 190 and a discrete Y-coordinate ("Y") along Y-axis 195. A smaller number of pixel detectors are shown in FIG. 1 for the sake of visual clarity. Detector 120 may be (a) centered on projection line 185 to enable full-fan imaging of target object 105, (b) offset from projection line 185 to enable half-fan imaging of target object 105, or (c) movable with respect to projection line 185 to allow both full-fan and half-fan imaging of target object 105.

Any suitable imaging modality or modalities may be used by the imaging system 100, such as computed tomography (CT), cone beam computed tomography (CBCT), etc. For example, CT involves imaging of the internal structure of a target object by collecting projection image data in a single scan operation ("scan"). CT is widely used in the medical field to view the internal structure of selected portions of the human body. CBCT is a 3D X-ray imaging technique in which the radiation beam is projected onto target object 105 with wide beam geometry to produce 2D projection image data. In general, the quality of CBCT images might be lower compared to CT images, such as due to limited field size. In both CT and CBCT, kiloVoltage (kV) imaging energy is generally used but megavoltage (mV) may be used in certain cases.

Figure 2A:
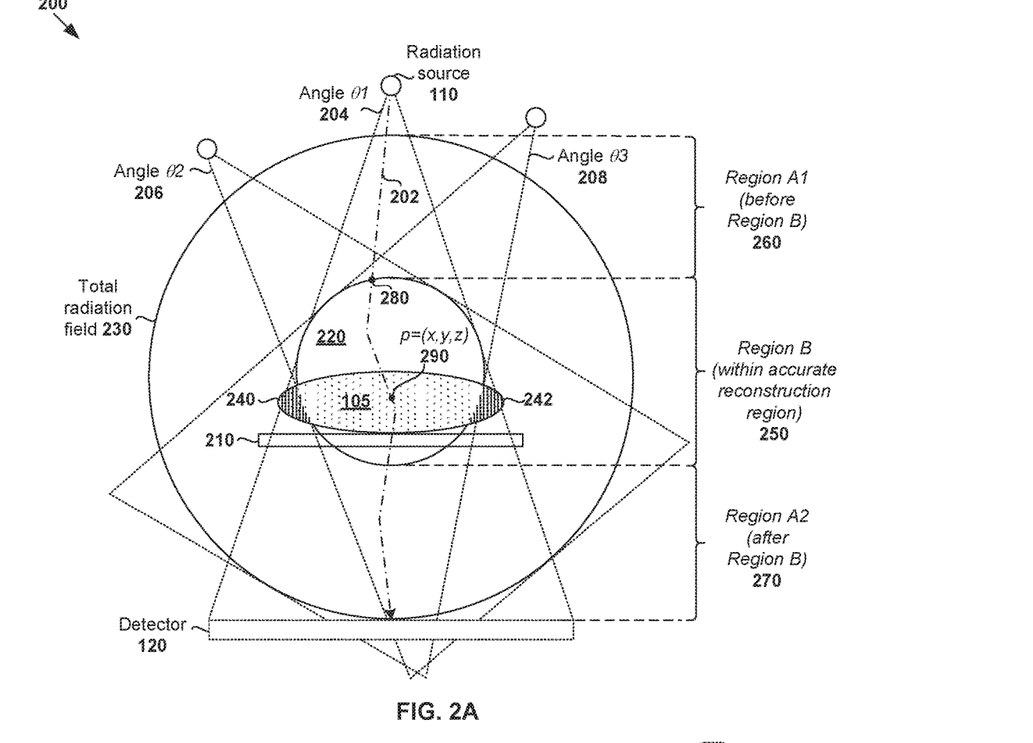
FIG. 2A is a schematic diagram illustrating a first view of an example configuration of a radiation source and a detector with respect to a target object.

An important aspect of radiotherapy treatment planning and delivery is dose estimation, which determines the level of radiation dose to be applied to a patient. Dose estimation relies on the accuracy of the projection image data of the patient. However, due to limitations of imaging system 100, the projection image data may be incomplete. An example is illustrated in FIG. 2A, which is a schematic diagram illustrating a first view of example configuration 200 of radiation source 110 and detector 120 with respect to target object 105. During imaging, radiation (see ray 202) is projected onto target object 105 (generally a patient, etc.) who lies on treatment couch 210. Radiation source 110 and detector 120 are rotated 360° about target object 105 to acquire projection image data at various projection angles (e.g., every 1°).

Figure 2B:
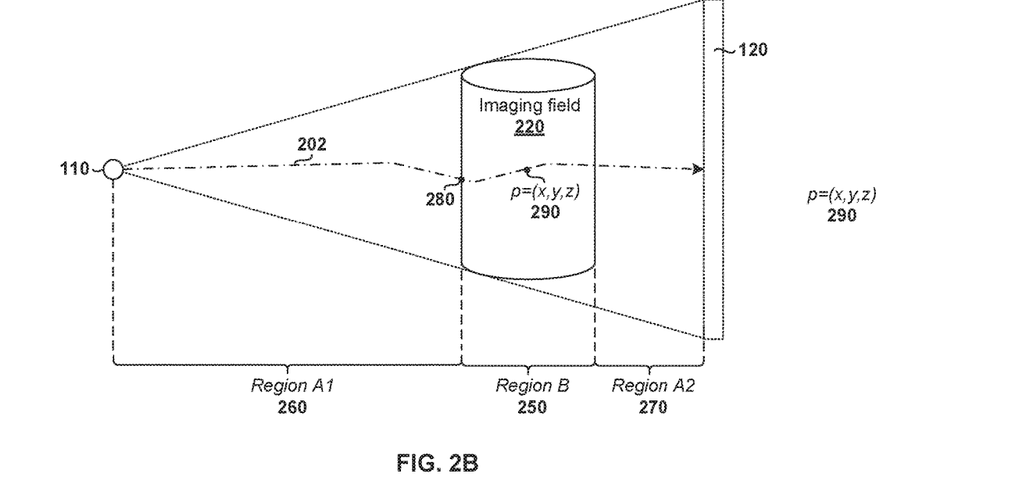
FIG. 2B is a schematic diagram illustrating a second view of the example configuration in FIG. 2A.

Due to the beam size of imaging system 100 and/or factor(s) such as the size of detector 120, accurate projection image data may only be reconstructed for a limited (cylindrical) region around the gantry rotation axis and does not necessarily cover the whole body of target object 105. In the example in FIG. 2A, such (accurate) region is represented as region "B" 250 within imaging field 220 that is fully irradiated and therefore visible in all different 2D projections. Another view of imaging field is shown in FIG. 2B, which is a schematic diagram illustrating a second view of the example configuration in FIG. 2A. As exemplified using FIGS. 2A and 2B, the term "imaging field" may refer generally to a volume (e.g., generally cylindrical volume 220) that is visible in all projections from different angles. Imaging field 220 may also be referred to as a substantially accurate (e.g., CBCT) reconstruction region.

In practice, imaging field 220 is generally smaller than total radiation field 230, which may refer generally to a total volume of interest radiated from at least one gantry angle. For this reason, any part of target object 105 that is not fully irradiated from all projection angles, because it is either fully or partially outside of imaging field 220 from at least some projection angles, will only be partially visible or not visible in the acquired projection image data. To illustrate this, three projection angles θ1 (see 204), θ2 (see 206) and θ3 (see 208) are shown in FIG. 2A, although projection image data may be acquired at additional or alternative angles in practice. At first angle θ1 (see 204), target object 105 is fully irradiated within imaging field 220. However, at other projection angles such as second angle θ2 (see 206), one part (see 240) of target object 105 is not fully irradiated. Similarly, at further projection angles such as third angle θ3 (see 208), another part (see 242) not fully irradiated. This means that some parts (e.g., 240, 242) of target object 105 will be included at certain projection angles, and excluded at others. The resulting projection image data will be incomplete for any regions outside of the accurate (e.g., CBCT) reconstruction region.

Conventionally, however, dose estimation generally requires accurate projection image data and reconstruction in the whole region where any field is entering target object 105 to a region of interest. In other words, accurate reconstruction is required for not only region "B" 250, but also other region(s) of total radiation field 230 where part(s) of target object 105 may not be fully irradiated. Since such accurate reconstruction is not always achievable, which makes it more difficult, if not impossible, to perform dose estimation using conventional approaches. This in turn adversely affects radiotherapy treatment planning and delivery.

Dose Estimation

According to examples of the present disclosure, improved dose estimation may be performed based on partially reconstructed volume image data (i.e., 3D) associated with region "B" 250, and a partition of projection image data (i.e., 2D) associated with region "A1" 260 located before region "B" 250. Given the often close proximity between tumors and proximal healthy structures (e.g., organs, etc.), any improvement in dose estimation has the potential of improving treatment outcome, such as increasing tumor control probability and/or reducing the likelihood of health complications or death due to radiation overdose in the healthy structures.

Figure 3:
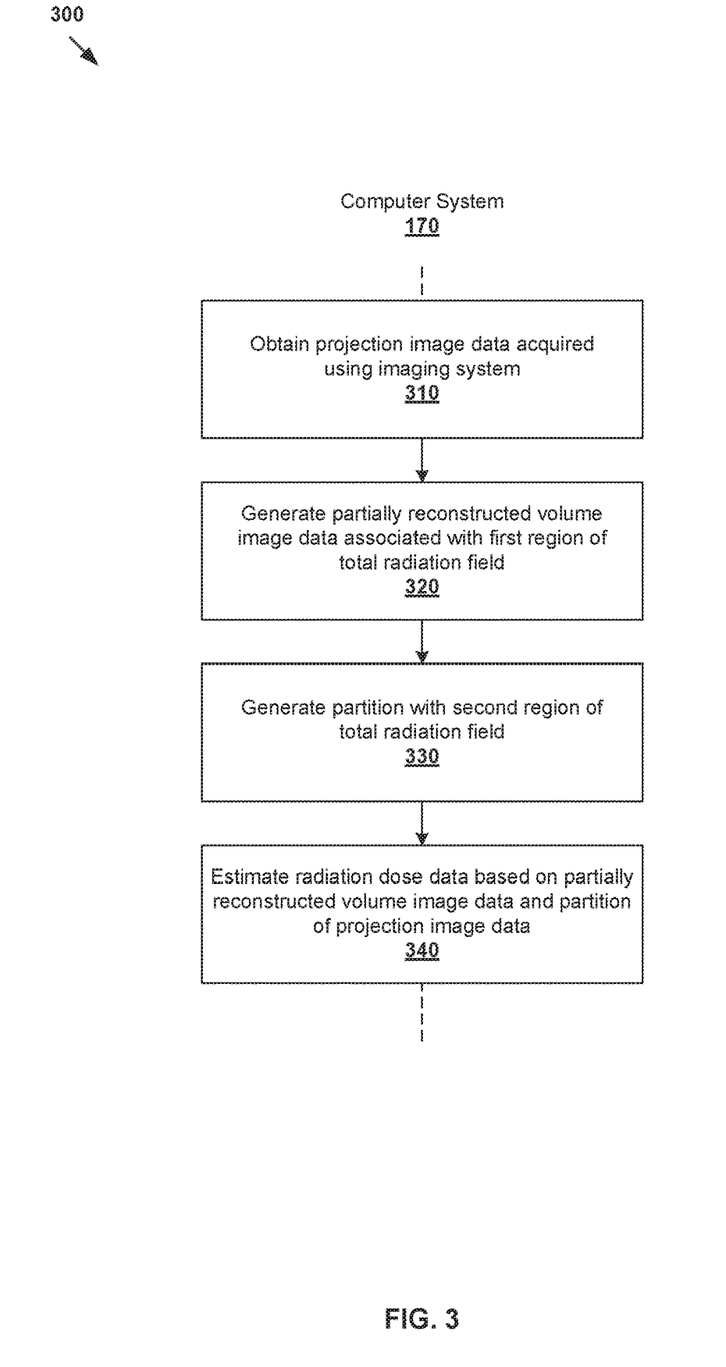
FIG. 3 is a flowchart of an example process for a computer system to perform radiation dose estimation for a target object.

In more detail, FIG. 3 is a flowchart of example process 300 for a computer system to perform radiation dose estimation for a target object. Example process 300 may include one or more operations, functions, or actions illustrated by one or more blocks, such as 310 to 340. The various blocks may be combined into fewer blocks, divided into additional blocks, and/or eliminated based upon the desired implementation. Example process 300 may be implemented using any suitable computer system, an example of which will be discussed using FIG. 7.

At 310 in FIG. 3, projection image data is obtained. The projection image data may be acquired using imaging system 100 by projecting radiation from radiation source 110 through target object 105 positioned within total radiation field 230 of imaging system 100. Here, the term "obtained" or "obtain" may refer to either receiving the projection image data (e.g., from controller 160) or retrieving it from a storage device (not shown for simplicity). The obtained projection image data may be pre-processed using any suitable techniques, defect pixel correction, scatter correction, dark field correction, beam hardening correction, etc.

At 320 in FIG. 3, partially reconstructed volume image data is generated from the projection image data. The partially reconstructed volume image data may be associated with a first region of total radiation field 230. In the example in FIG. 2A and FIG. 2B, the "first region" is represented using region "B" 250 in which part(s) of target object 105 are fully irradiated from all projection angles.

At 330 in FIG. 3, a partition of the projection image data is generated. The partition may be associated with a second region of total radiation field 230 that is located before the first region from a direction of radiation source 110. In the example in FIG. 2A and FIG. 2B, the "second region" is represented using region "A1" 260 in which part(s) of target object 105 are not fully irradiated from all projection angles (i.e., partially irradiated from some projection angles).

At 340 in FIG. 3, radiation dose data for target object 105 may be estimated based on the partially reconstructed volume image data associated with first region "B" 250 and the partition associated with second region "A1" 260.

As will be described further using FIG. 4, dose estimation may be performed at block 340 in FIG. 3 using any suitable approach, such as algorithms that are based on a radiological distance a ray (in treatment beam) has travelled in tissue before a particular point at which dose data is estimated. Such algorithms (e.g., pencil beam convolution, etc.) generally have clinically-accepted accuracy. In this case, block 340 in FIG. 3 may involve, based on the partition associated with second region "A1" 260, determining a radiological distance that specifies a radiological distance a ray from radiation source 110 travels in second region "A1" 260 before entering into first region "B" 250 via an entry point (see 280 in FIG. 2A and FIG. 2B).

Further, based on the partially reconstructed volume image data, block 340 in FIG. 3 may involve determining a radiological distance associated with first region "B" 250 that specifies a radiological distance the ray travels in first region "B" 250 from the entry point (see 280 in FIG. 2A and FIG. 2B) to a particular point (see 290 in FIG. 2A and FIG. 2B) within target object 105. In this case, the radiation dose value at that particular point may be estimated based on a total of the radiological distance associated with first region "B" 250 and the radiological distance associated with second region "A1" 260 (i.e., total radiological distance).

In the following, various examples will be discussed using FIG. 4 to FIG. 7. In particular, example dose estimation using FIG. 4, FIG. 5A and FIG. 5B, improved radiotherapy treatment planning based on the dose estimation using FIG. 6, and example computer system using FIG. 7.

Image Partitioning

Figure 4:
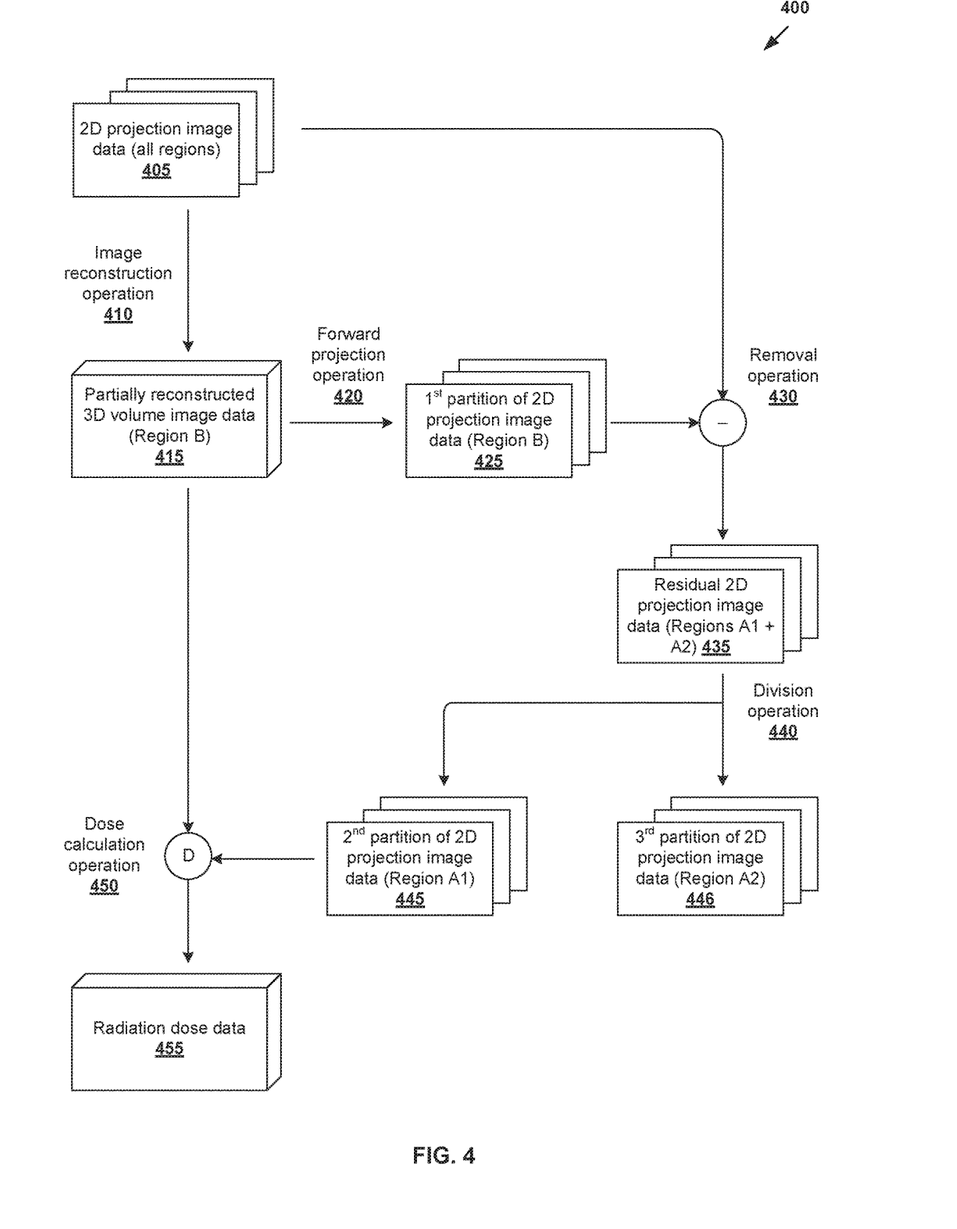
FIG. 4 is a flowchart of an example detailed process for a computer system to perform radiation dose estimation for a target object.

FIG. 4 is a flowchart illustrating example detailed process 400 for a computer system to perform radiation dose estimation for a target object. Example process 400 may include one or more operations, functions, actions or data items illustrated by one or more blocks, such as 405 to 455. The various blocks may be combined into fewer blocks, divided into additional blocks, and/or eliminated based upon the desired implementation. Similar to the example in FIG. 3, example process 400 may be implemented using any suitable computer system, an example of which will be discussed using FIG. 7.

At 410 in FIG. 4, partially reconstructed volume image data 415 is generated by performing an image reconstruction operation on projection image data 405 acquired using imaging system 100. As discussed using FIG. 2A and FIG. 2B, partially reconstructed volume data 415 is associated with first region "B" 250, which may be referred to as an "accurate" region because it is fully irradiated and visible in projection image data 405 acquired from different projection angles.

In contrast, when moving further away from first region "B" 250, less and less projection image data is available in second region "A1" 260 and third region "A2" 270. Second region "A1" 260 is located before imaging field 220 from the direction of radiation source 110. Third region "A2" 270 is located after imaging field 220 from the direction of radiation source 110. Any suitable reconstruction algorithm may be used to perform reconstruction operation 410 for first region "B" 250, such as non-iterative reconstruction (e.g., filtered back projection), iterative reconstruction (e.g., algebraic and statistical based reconstruction), etc.

At 420, 430 and 440 in FIG. 4, image partitioning is performed to partition projection image data 405 into three partitions 425, 445, 446. Here, the term "partition" may refer generally to a portion of projection image data 405. For example, if a particular value (x) includes multiple (N>1) components, such as $x=x_1+ \ldots +x_N$, a "partition" of the value may be one or some of the multiple components. First partition 425 includes attenuation contribution from first region "B" 250, second partition 445 from in second region "A1" 260 and third partition 446 from third region "A2" 270.

In more detail, first partition 425 may be generated from partially reconstructed volume image data 415 by performing forward projection operation 420 for first region "B" 250. Here, "forward projection" may refer generally to a transformation from the volume space to the projection space. Forward projection (also known as synthesizing projection data) may include data such as attenuation path integrals (primary signal), Rayleigh scatter and Compton scatter. Forward projection operation 420 may be monochromatic or polychromatic; source-driven or destination-drive; voxel-based or blob-based; and use Ray Tracing, Monte Carlo or any suitable finite element approaches.

At 420 and 430 in FIG. 4, second partition 445 and third partition 446 may be generated by removing the contribution of first region "B" 250 from projection image data 405, and then dividing the resulting "residual" projection image data 435 (i.e., includes the contribution from "A1" 260 and "A2" 270) into second partition 445 and third partition 446.

In practice, any suitable algorithms may be used to generate partitions 425, 445, 446. For example, based on attenuation law, a pixel value in projection image data 405 is approximately $e^{-\lambda D}$, where D is the total mass (or integrated electron density) along a ray associated with that particular pixel value, and $\lambda$ represents the photon mean free path. In general, the term "electron density" represents the number of electrons in a medium per unit volume. The electron density is important for dose estimation because, during X-ray interaction process (Compton scattering), a photon interacts with electrons in the absorbing medium, and the probability of interaction is proportional to the electron density.

Image partitioning according to 420, 430 and 440 in FIG. 4 may be performed to partition projection image data 405 into the following:

$$D = D_{A1} + D_B + D_{A2}. \quad (1)$$

In equation (1), $D_{A1}$ is the total mass along the ray in second region "A1" 260, $D_B$ is the total mass along the ray in first region "B" 250, $D_{A2}$ is the total mass along the ray in third region "A2" 270 and D is the total mass in all three regions. In this case, removal operation 430 may be involve subtracting $D_B$ from D, such as by integrating electron density along a ray from partially reconstructed volume image data 415 in first partition 425.

After the contribution from first region "B" 250 is removed, residual projection image data 435 (i.e., $D - D_B = D_{A1} + D_{A2}$) includes the contribution from "A1" 260 (i.e., front image) and that from "A2" 270 (i.e., back image). Division operation 440 may then be performed to divide residual projection image data 435 into $D_{A1}$ and $D_{A2}$. One simple approach may involve dividing residual projection image data 435 into second partition 445 and third partition 446 evenly (e.g., using appropriate masking). Other example approaches are illustrated in FIG. 5A and FIG. 5B.

Figure 5A:
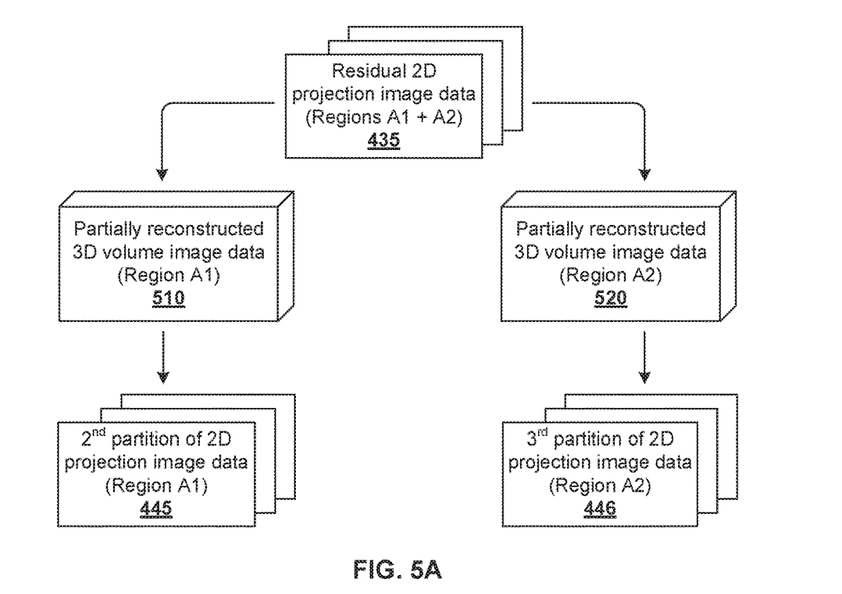
FIG. 5A is a flowchart of a first example process for generating partitions of residual projection image data.
Figure 5B:
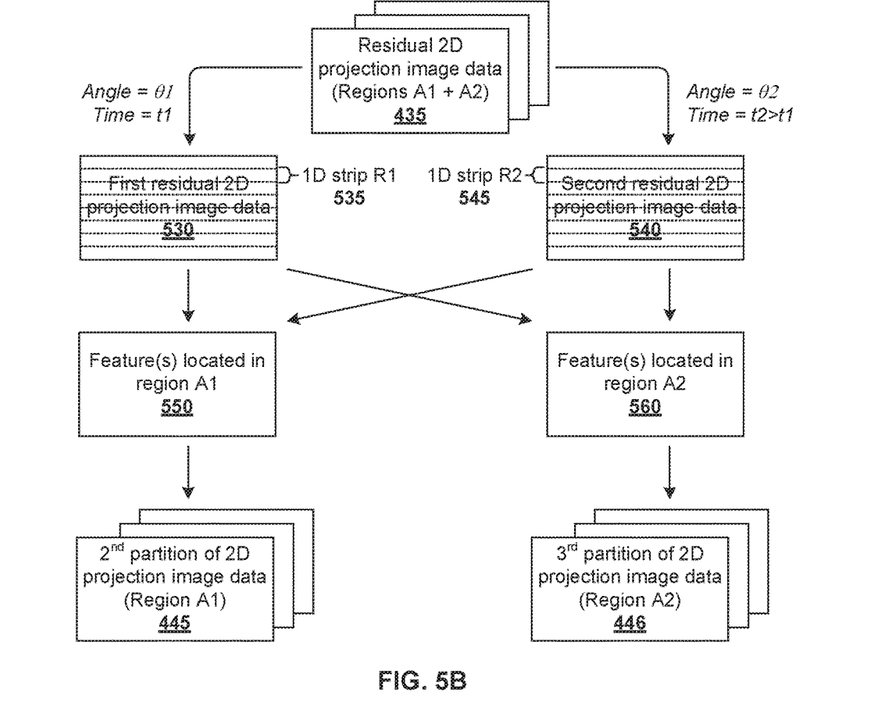
FIG. 5B is a flowchart of a second example process for generating partitions of residual projection image data.

FIG. 5A is a flowchart of a first example process for generating partitions 445, 446 of residual projection image data 435. In this case, residual projection image data 435 is used to generate two sets of partially reconstructed volume image data associated with respective regions "A1" 260 and "A2" 270. Even though the reconstruction is generally inaccurate due to incomplete data in those regions, it can be used to determine an electron density integral along the ray in regions "A1" 260 and "A2" 270 to reconstruct respective $D^*_{A1}$ and $D^*_{A2}$, which are approximations of the respective $D_{A1}$ and $D_{A2}$.

As shown in FIG. 5A, first partially reconstructed volume image data 510 ($D^*_{A1}$) is associated with second region "A1" 260 while second partially reconstructed volume image data 520 ($D^*_{A2}$) is associated with third region "A2" 270. Residual projection image data 435 may then be divided into second partition 445 ($D_{A1}$) and third partition 446 ($D_{A2}$) based on the following ratio associated with $D^*_{A1}$ and $D^*_{A2}$: As such, using the example in FIG. 5A, a low quality 3D reconstruction may be used to determine $D^*_{A1}$ and $D^*_{A2}$, which are then corrected to respective $D_{A1}$ and $D_{A2}$.

$$D_{A1} = D^*_{A1}\left(\frac{D_{A1} + D_{A2}}{D^*_{A1} + D^*_{A2}}\right) \text{ and } D_{A2} = D^*_{A2}\left(\frac{D_{A1} + D_{A2}}{D^*_{A1} + D^*_{A2}}\right). \quad (2)$$

FIG. 5B is a flowchart of a second example process for generating partitions 445, 446 of residual projection image data 435. In this case, two different sets of consecutive residual projection image data acquired at respective projection angles $\theta 1$ and $\theta 2$, with angular separation $\theta_{diff} = \theta 2 - \theta 1$. For example, first residual projection image data 530 may be acquired at projection angle=$\theta 1$ and time=t1, and second residual projection image data 540 at $\theta 2$ and t2>t1 according to a gantry rotation from left to right.

As will be explained further below, a comparison between first residual projection image 530 and second residual projection image data 540 may be performed to generate second partition 445 and third partition 446. For example, when there is little angular separation between two images, they may be considered as a "stereographic pair." Looking at sharp features (e.g., bone structures) in the stereographic pair, it is possible (to some extent) to recognize which sharp features belong to the front image and which belong to the back image. Defining a 2D deformation field between the stereographic pair, the features may be distinguished for the two different regions based on their movement.

To identify the relevant features in the example in FIG. 5B, a one-dimensional (1D) image strip R1 (see 535) from first residual projection image data 530 may be compared against a corresponding image strip R2 (see 545) from second residual projection image data 540. Both strips R1 and R2 describe the projection from the same volume. Based on strips R1 and R2, features (see 550) that seem to be moving left in R2 when compared to R1 may be identified to be located within second region "A1" 260 (i.e., before the isocenter of imaging field 220). In contrast, features (see 560) that seem to be moving right in R2 compared to R1 may be identified to be located within third region "A2" 270 (i.e., after the isocenter of imaging field 220).

Any suitable algorithmic solution may be performed to split a particular image strip R (i.e., a 1D vector of pixel values) into its $R_{A1}$ and $R_{A2}$ components such that $R = R_{A1} + R_{A2}$ and the following is minimized:

$$L2[S_L(R_{A1}) + S_R(R_{A2})] \quad (3)$$

In equation (3), L2-norm (L2) represents an error measure, and may contain a weighting term proportional to the absolute value of a gradient (e.g., to reduce degeneracy of areas where the pixel values are uniform). Shift operators $S_L$ and $S_R$ are moving elements in image strip R that move to the left or right (e.g., with a predetermined amount of movement). The size of the shift operators may be proportional to the radius of imaging field 220 and to $\tan(\theta_{diff})$. The above may be repeated for each and every image strip R to obtain corresponding $R_{A1}$ and $R_{A2}$. Second partition 445 may be then generated based on $R_{A1}$, and third partition 446 based on $R_{A2}$.

Note that the terms "left" and "right" in the above examples are relative to the direction of the gantry rotation from left to right. If the opposite direction is considered (i.e., gantry rotation from right to left), features located within second region "A1" 260 may be moving against the direction of the gantry rotation (i.e., left to right) in R2 compared to R1, while second features located within third region "A2" 270 may be moving in the same direction of the gantry rotation (i.e., right to left). In practice, first residual projection image data 530 and second residual projection image data 540 may also be opposing sets instead of being a stereographic pair.

Dose Estimation

Referring to FIG. 4 again, dose calculation operation 450 (labelled "D") may be performed to generate radiation dose data 455 based on partially reconstructed volume image data 415 associated with first region "B" 250 and second partition 445 associated with second region "A1" 260. Any suitable algorithm may be used for dose calculation, such as pencil beam convolution algorithm, etc. In practice, a "pencil beam" may refer generally to a beam of electrons of a small cross-sectional area. The radiation dose for an irregular field F may be obtained by convolving a field density distribution with a pencil beam kernel. Analytically, the radiation dose value at a particular point p=(x, y, z) may be expressed as follows:

$$D(x, y, z; F) = \frac{(f + z_{ref})^2}{(f + z)^2} \int_{-\infty}^{\infty} \int_{-\infty}^{\infty} F(u, v) P_{int}(u, v, z) K(x - u, y - v, z) du dv. \quad (4)$$

In equation (4), f is the source-to-surface distance (SSD), F(x, y) the field intensity function, $P_{int}(x, y, z)$ the intensity profile, K(x, y, z) is the pencil beam kernel, and $z_{ref}$ the reference depth used for normalization. F(x, y) describes field blocking in that it is unity for points inside the field opening, and zero or a user-given transmission factor through the beam limiting device outside the field. The intensity profile $P_{int}(x, y, z)$ accounts for the variation of the primary photon fluence as a function of off-axis distance and depth. The pencil beam kernel K(x, y, z) describes the dose distribution of a very narrow beam entering a water phantom along the z-axis. The functions $P_{int}(x, y, z)$ and K(x, y, z) may be derived from measured beam data of several square field sizes. Any suitable approach may be used to solve the To account for tissue heterogeneities in target object 105, a heterogeneity correction may be determined based on a radiological (effective) distance or thickness $d_{eff}$ that is defined as an integral of density along a ray from a body surface of target object 105 to the current density as follows:

$$d_{eff} = \frac{1}{\rho_{water}} \int_0^d \rho(z) dz. \quad (5)$$

In equation (5), d is the geometrical depth, ρ(z) the density at depth z and $\rho_{water}$ the density of water. The densities may be estimated from projection image data 405 (e.g., CT or CBCT images). Thus, to determine the inhomogeneity correction inside first region "B" 250, $d_{eff}$ may be calculated by determining by integrating electron density along the ray in second region "A1" 260 based on second partition 445, and then integrating electron density along the ray in first region "B" 250 based on partially reconstructed volume image data 415 from the point where the ray enters first region "B" 250 to a particular point where the dose is estimated.

Referring to the example in FIG. 2A and FIG. 2B again, based on second partition 445, a radiological distance that ray 202 travels in second region "A1" 260 before entering into first region "B" 250 via an entry point (see 280) may be determined. Further, based on partially reconstructed volume image data 415, a radiological distance that ray 202 travels in first region "B" 250 from the entry point (see 280) to a particular (3D) point p=(x, y, z) within target object 105 (see 290) may be determined. The total radiological distance (i.e., sum of the distances in second region "A1" 260 and first region "B" 250) may be used to estimate the radiation dose value at p=(x, y, z). For example, using pencil beam approximation, the total radiological distance may be used to read from a depth dose curve the amount of radiation dose to be delivered to the patient.

In the above examples, third partition 446 associated with third region "A2" 270 may be ignored during dose calculation because the attenuation in this region generally does not affect the dose distribution significantly. First partition associated with first region "B" 250 may also be ignored because its associated 3D volume image data (i.e., partially reconstructed volume image data 415) may be used for dose estimation instead. The dose estimation approach according to example of the present disclosure may be suitable for use in imaging system 100 with Flattening-Filter-Free beam where the amount of non-focal radiation is generally small.

Improved Radiotherapy Treatment

Radiation dose data 455 estimated according to examples of the present disclosure may be used to improve radiotherapy treatment, particularly to check and/or improve a treatment plan of a patient. An example is shown in FIG. 6, which is a schematic diagram illustrating improved radiotherapy treatment planning process 600 using radiation dose data estimated using the example in FIG. 4.

Prior to a treatment session (see 602), image acquisition is performed using imaging system 100 for a patient requiring radiotherapy treatment. The aim is to acquire projection image data (see 610) based on which a treatment plan (see 620) is devised for the patient. In practice, treatment planning may be performed based on goal doses prescribed by a clinician (e.g., oncologist, dosimetrist, treatment planner, etc.), such as based on the clinician's experience, the type and extent of the tumor, patient geometry and condition, etc. Further, the capabilities and limitations of the radiotherapy treatment system are also considered during treatment planning.

Figure 6:
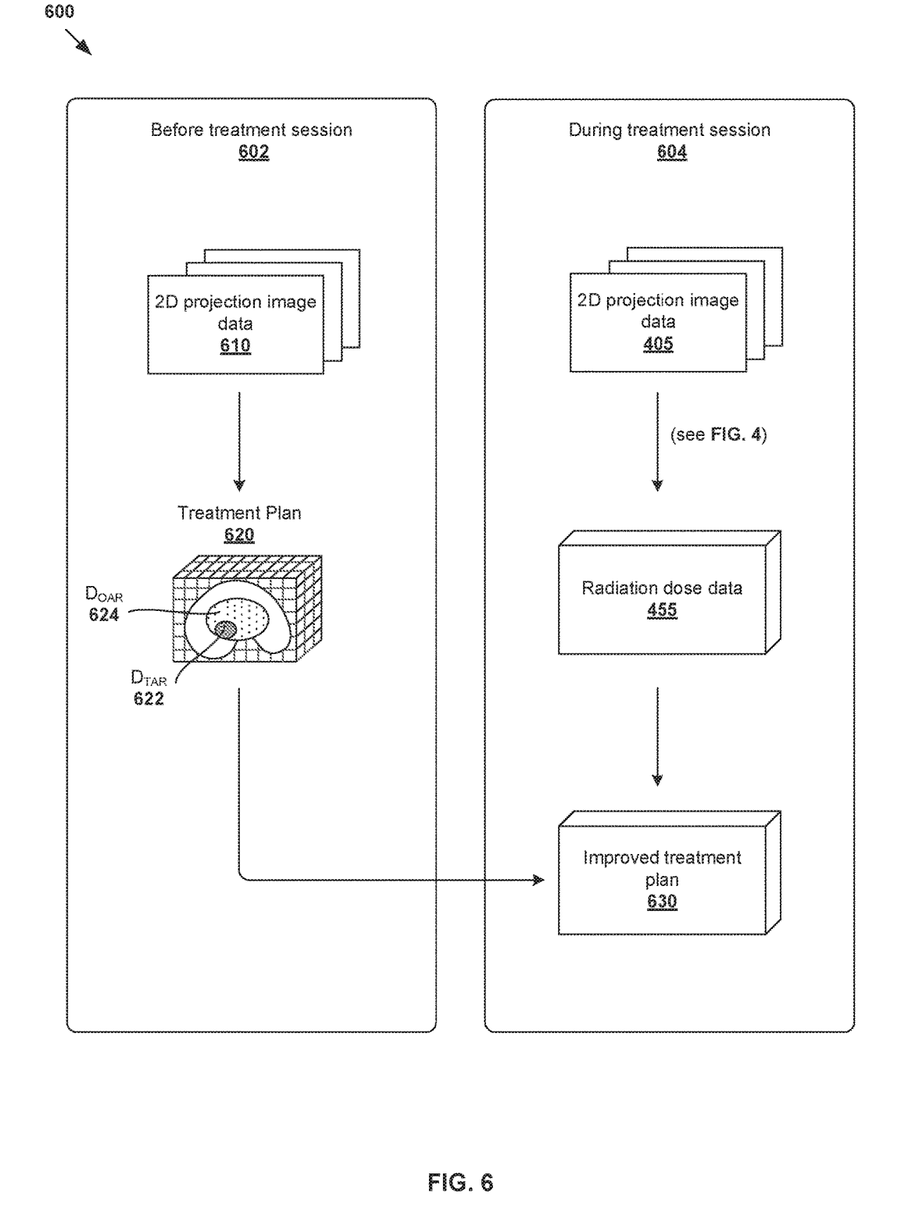
FIG. 6 is a schematic diagram illustrating an improved radiotherapy treatment planning process using radiation dose data estimated using the example in FIG. 4.

In the example in FIG. 6, treatment plan 620 defines the radiation dose to be delivered to the patient's anatomy (also known as a treatment volume). Radiation dose labelled "$D_{TAR}$" (see 622) represents the dose level for a target, which may represent a malignant tumor (e.g., prostate tumor, brain tumor, etc.) requiring radiotherapy treatment. Radiation dose labelled "$D_{OAR}$" (see 624) represents the dose level for any adjacent organ-at-risk (OAR), which represents a proximal healthy structure (e.g., rectum, bladder, optic nerve, brain stem, etc.) that might be adversely affected by the treatment. A higher goal dose is generally prescribed for a target and a lower goal dose for an OAR. A dose-volume histogram (DVH) may be used to summarize 3D dose distributions in a graphical two-dimensional (2D) format.

During a treatment session (see 604) where radiotherapy treatment is delivered to the patient, treatment plan 620 may be improved using radiation dose data 455 estimated according to examples of the present disclosure. For example, this may involve comparing treatment plan 620 with radiation dose data 455 to account for the current positioning of the patient during the treatment session and possible changes in the patient's anatomy since projection image data (see 610) was last acquired. Based on the comparison, possible improvements may be made to treatment plan 620 (see improved treatment plan 630) before radiotherapy treatment is delivered.

In another example, the comparison may be made to identify one or more differences between radiation dose data 455 obtained at treatment time and treatment plan 620 designed at planning time. Based on the comparison, a decision may be made as to whether to proceed with the treatment. Alternatively, multiple candidate treatment plans may be generated at treatment time, and the candidate that 'best' matches with treatment plan 620 may be selected based on any suitable criteria for treatment purposes. Adaptive treatment may also be performed to alter treatment plan 620 at treatment time.

Computer System

Figure 7:
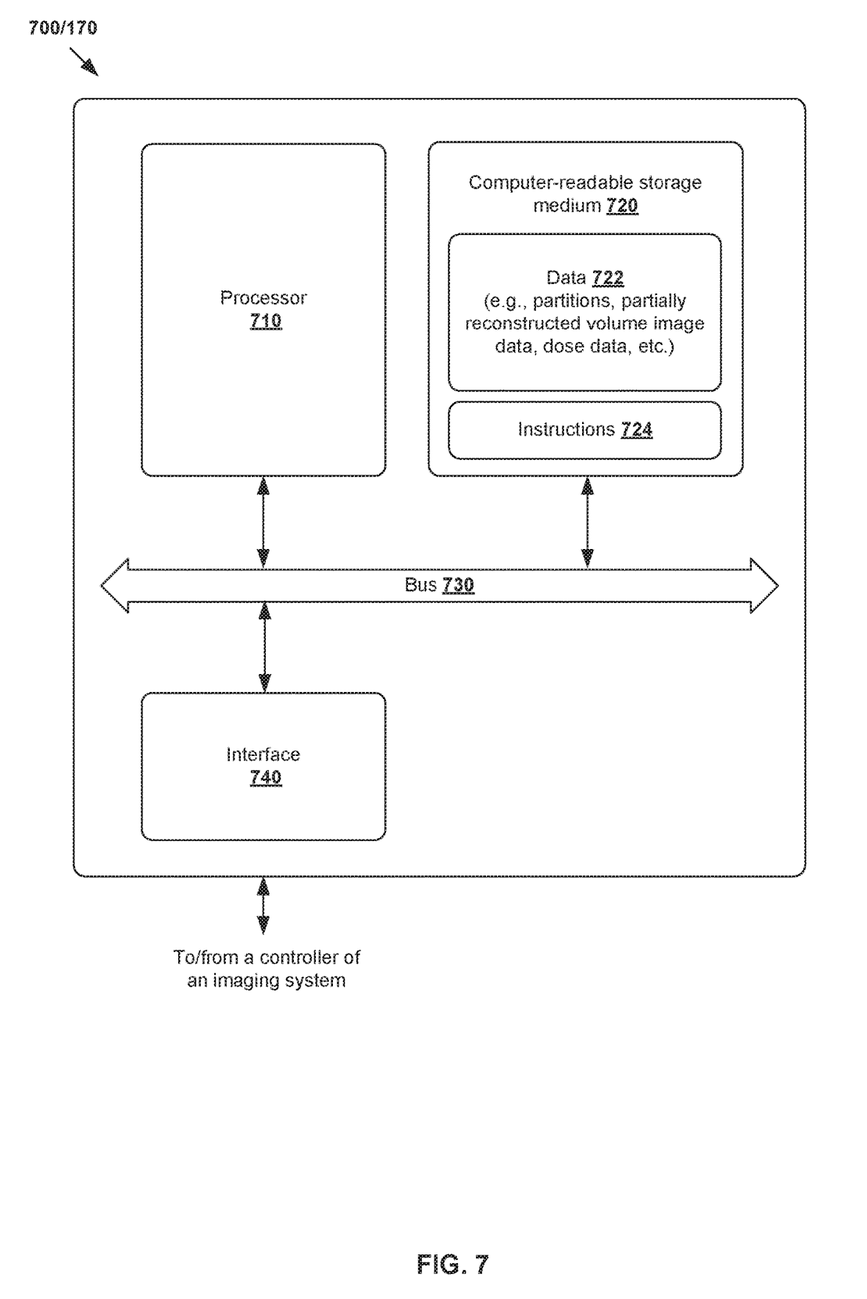
FIG. 7 is a schematic diagram of an example computer system to perform radiation dose estimation for a target object.

The above examples can be implemented by hardware, software or firmware or a combination thereof. FIG. 7 is a schematic diagram of example computer system 700/170 to perform radiation dose estimation for target object 105. In this example, computer system 700/170 may include processor 710, computer-readable storage medium 720, interface 740 to interface with a radiotherapy treatment system (e.g., same machine as imaging system 100), and bus 730 that facilitates communication among these illustrated components and other components.

Processor 710 is to perform processes described herein with reference to FIG. 1 to FIG. 6. Computer-readable storage medium 720 may store any suitable data 722, such as various data 405/415/425/435/445/446/455 discussed, etc. Computer-readable storage medium 720 may further store computer-readable instructions 724 which, in response to execution by processor 710, cause processor 710 to perform processes described herein.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

We claim:

1. A method for a computer system to perform radiation dose estimation for a target object, the method comprising:
obtaining projection image data acquired using an imaging system, wherein the projection image data is acquired by projecting radiation from a radiation source through the target object positioned within a total radiation field of the imaging system;
generating partially reconstructed volume image data based on the projection image data, wherein the partially reconstructed volume image data is associated with a first region within the total radiation field;
generating a partition of the projection image data, wherein the partition is associated with a second region of the total radiation field that is located before the first region from a direction of the radiation source; and
estimating radiation dose data for the target object based on the partially reconstructed volume image data associated with the first region and the partition associated with the second region.

2. The method of claim 1, wherein estimating the radiation dose data comprises:
based on the partition of the projection image data, determining a radiological distance associated with the second region that specifies a radiological distance a ray from the radiation source travels in the second region before entering into the first region.

3. The method of claim 2, wherein estimating the radiation dose data comprises:
based on the partially reconstructed volume image data, determining a radiological distance associated with the first region that specifies a radiological distance the ray travels in the first region to a particular point within the target object at which a radiation dose value is estimated.

4. The method of claim 3, wherein estimating the radiation dose data comprises:
estimating the radiation dose value at the particular point based on a total of the radiological distance associated with the first region and the radiological distance associated with the second region.

5. The method of claim 1, wherein generating the partition of the projection image data comprises:
based on partially reconstructed volume image data, generating residual projection image data that includes the partition associated with the second region and a partition associated with a third region of the total radiation field that is located after the first region from the direction of the radiation source.

6. The method of claim 5, wherein generating the partition of the projection image data comprises:
based on a ratio, dividing the residual projection image data into the partition associated with the second region and the partition associated with the third region.

7. The method of claim 5, wherein generating the partition of the projection image data comprises:
comparing first residual projection image data associated with a first angle of the radiation source and second residual projection image data associated with a second angle of the radiation source; and
based on the comparison, generating the partition associated with the second region and the partition associated with the third region.

8. A non-transitory computer-readable storage medium that includes a set of instructions which, in response to execution by a processor of a computer system, cause the processor to perform a method of radiation dose estimation, the method comprising:
obtaining projection image data acquired using an imaging system, wherein the projection image data is acquired by projecting radiation from a radiation source through the target object positioned within a total radiation field of the imaging system;
generating partially reconstructed volume image data based on the projection image data, wherein the partially reconstructed volume image data is associated with a first region within the total radiation field;
generating a partition of the projection image data, wherein the partition is associated with a second region of the total radiation field that is located before the first region from a direction of the radiation source; and
estimating radiation dose data for the target object based on the partially reconstructed volume image data associated with the first region and the partition associated with the second region.

9. The non-transitory computer-readable storage medium of claim 8, wherein estimating the radiation dose data comprises:

based on the partition of the projection image data, determining a radiological distance associated with the second region that specifies a radiological distance a ray from the radiation source travels in the second region before entering into the first region.

10. The non-transitory computer-readable storage medium of claim 9, wherein estimating the radiation dose data comprises:
based on the partially reconstructed volume image data, determining a radiological distance associated with the first region that specifies a radiological distance the ray travels in the first region to a particular point within the target object at which a radiation dose value is estimated.

11. The non-transitory computer-readable storage medium of claim 10, wherein estimating the radiation dose data comprises:
estimating the radiation dose value at the particular point based on a total of the radiological distance associated with the first region and the radiological distance associated with the second region.

12. The non-transitory computer-readable storage medium of claim 8, wherein generating the partition of the projection image data comprises:
based on partially reconstructed volume image data, generating residual projection image data that includes the partition associated with the second region and a partition associated with a third region of the total radiation field that is located after the first region from the direction of the radiation source.

13. The non-transitory computer-readable storage medium of claim 12, wherein generating the partition of the projection image data comprises:
based on a ratio, dividing the residual projection image data into the partition associated with the second region and the partition associated with the third region.

14. The non-transitory computer-readable storage medium of claim 12, wherein generating the partition of the projection image data comprises:
comparing first residual projection image data associated with a first angle of the radiation source and second residual projection image data associated with a second angle of the radiation source; and
based on the comparison, generating the partition associated with the second region and the partition associated with the third region.

15. A computer system configured to perform radiation dose estimation, the computer system comprising: a processor and a non-transitory computer-readable medium having stored thereon instructions that, when executed by the processor, cause the processor to:
obtain projection image data acquired using an imaging system, wherein the projection image data is acquired by projecting radiation from a radiation source through the target object positioned within a total radiation field of the imaging system;
generate partially reconstructed volume image data based on the projection image data, wherein the partially reconstructed volume image data is associated with a first region within the total radiation field;
generate a partition of the projection image data, wherein the partition is associated with a second region of the total radiation field that is located before the first region from a direction of the radiation source; and
estimate radiation dose data for the target object based on the partially reconstructed volume image data associated with the first region and the partition associated with the second region.

16. The computer system of claim 15, wherein instructions for estimating the radiation dose data cause the processor to:
based on the partition of the projection image data, determine a radiological distance associated with the second region that specifies a radiological distance a ray from the radiation source travels in the second region before entering into the first region.

17. The computer system of claim 16, wherein instructions for estimating the radiation dose data cause the processor to:
based on the partially reconstructed volume image data, determine a radiological distance associated with the first region that specifies a radiological distance the ray travels in the first region to a particular point within the target object at which a radiation dose value is estimated.

18. The computer system of claim 17, wherein instructions for estimating the radiation dose data cause the processor to:
estimate the radiation dose value at the particular point based on a total of the radiological distance associated with the first region and the radiological distance associated with the second region.

19. The computer system of claim 15, wherein instructions for generating the partition of the projection image data cause the processor to:
based on partially reconstructed volume image data, generating residual projection image data that includes the partition associated with the second region and a partition associated with a third region of the total radiation field that is located after the first region from the direction of the radiation source.

20. The computer system of claim 19, wherein instructions for generating the partition of the projection image data cause the processor to:
based on a ratio, dividing the residual projection image data into the partition associated with the second region and the partition associated with the third region.

21. The computer system of claim 19, wherein instructions for generating the partition of the projection image data cause the processor to:
comparing first residual projection image data associated with a first angle of the radiation source and second residual projection image data associated with a second angle of the radiation source; and
based on the comparison, generating the partition associated with the second region and the partition associated with the third region.

* * * * *